United States Patent [19]
Propper

[11] Patent Number: 5,419,701
[45] Date of Patent: May 30, 1995

[54] ENDOSTEAL DENTAL IMPLANT WITH SUPPLEMENTARY STABILIZER

[76] Inventor: Robert H. Propper, 401 N. Garfield, Alhambra, Calif. 91801

[21] Appl. No.: 810,970

[22] Filed: Dec. 19, 1991

[51] Int. Cl.⁶ .................................................. A61C 8/00
[52] U.S. Cl. ......................................... 433/173; 623/16
[58] Field of Search ............... 433/173, 175, 191, 192, 433/193, 194, 195; 623/16

[56] References Cited

U.S. PATENT DOCUMENTS

| | | | |
|---|---|---|---|
| 2,271,387 | 10/1955 | Aschuckian | 433/173 |
| 3,979,828 | 9/1976 | Taylor | 433/175 |
| 4,492,577 | 1/1985 | Farris et al. | 433/173 X |
| 4,552,532 | 11/1985 | Muzsary | 433/173 |
| 4,773,858 | 9/1988 | Marquez | 433/173 |
| 5,004,422 | 4/1991 | Propper | 433/173 X |
| 5,006,070 | 4/1991 | Komatsu | 433/173 X |
| 5,064,374 | 11/1991 | Lundgren | 433/173 |
| 5,094,618 | 3/1992 | Sullivan | 433/173 |

FOREIGN PATENT DOCUMENTS 0024008 2/1981 European Pat. Off. ............ 433/173
2357233 7/1977 France .

OTHER PUBLICATIONS

Translation of France 2,357,233.

Primary Examiner—David Isabella
Attorney, Agent, or Firm—Donald D. Mon

[57] ABSTRACT

This invention comprises a post for supporting dental superstructures. There are a set of legs integral with the post. The legs are structured to fit into cavities formed in the bony structure and become osseointegrated with the bone. This dental prosthesis provides attachment structures for attaching a bridge or other superstructures, or to form a portion of the superstructures.

9 Claims, 1 Drawing Sheet

ENDOSTEAL DENTAL IMPLANT WITH SUPPLEMENTARY STABILIZER

FIELD OF THE INVENTION

This invention relates to the field of dental prostheses and especially to a stabilized support which is osseointegrated with the bone of the jaw to provide means for attaching a bridge or other prosthetic superstructures, or to form a portion of them.

BACKGROUND OF THE INVENTION

Dental implants have developed into a well established art. When an appropriate implant is properly installed, the patient can expect many years of comfortable and effective service.

There are two principal classes of dental implants. One is the subperiosteal implant which surmounts the bony structure with a post or posts rising from it to support a bridge or denture. The objective is for this implant to become attached to the bone by tissue ingrowth. It does not enter into the bone structure. This class of implant does have some successes, but its potential for success, and its applicability to many operative conditions are less than one would desire.

The other class of implant is the endosteal implant which is inserted into the bony structure. In some endosteal implants, blades or anchors are sometimes provided, especially when osseointegration is not expected to occur. This is the situation where the material of construction is such that it does not become osseointegrated.

It has been learned that osseointegration can and does occur when the implant is made of or surfaced with titanium and its alloys. It also occurs when the material is coated with hydroxylapetite (HA). However, unless the material is titanium, the risk exists that the HA may vanish, and that the implant will later be lost because the underlying material did not osseointegrate.

U.S. Pat. No. 5,004,422 issued to Robert H. Propper, the inventor describes implants that are made of titanium or that are coated with HA, and a method for implanting them. This patent is incorporated herein in its entirety for its showing of such implants and of suitable materials, properties, and installations for osseointegration. The disclosures in this patent are directly applicable to the instant invention.

Implants according to the Propper patent function well for many persons. For other persons, neither the Propper implant nor any other osseointegrated implant known to the present inventor will serve. For example, in many patients the mandibular nerve in the lower jaw is too close to the surface of the bone structure to permit an implant of suitable length (depth) to be implanted. This is because the operative recess is too shallow to receive a long enough implant to be successfully osseointegrated without contacting the mandibular nerve. Any contact with the mandibular nerve can lead to numbness or a burning sensation of the lip and chin, both potentially permanent. Many patients are experiencing this numbness because of nerve injury caused by the repositioning procedure necessary for the implantation to be made.

In the upper jaw, the maxillary sinus is the problem. The sinus is best not entered, and taking an impression of a socket that is in communication with the sinus in the upper jaw is to be discouraged. The upper jaw of many patients does not provide enough bone sufficiently remote from the sinus to allow the use of an implant whose shape relates to that of a tooth with a single root, or with multiple roots.

It is an object of this invention to provide an osseointegratable implant with supplementary stabilizer means which themselves will osseointegrate. Then the main portion of the implant-conforming to an operative recess of relatively shallow depth can be quite short, and can be implanted in such very shallow recesses with no risk to the mandibular nerve or to the maxillary sinus, while still making an acceptable implant. Of course it is necessary to provide an implant which can be fitted into the operative recess. This is nor necessarily as simple as it sounds. For a single-root tooth, the socket from which it was extracted is often used for the recess. However, multiply-rooted molars whose roots diverge present an entirely different problem. Even such a tooth which was extracted could not usually be reinserted into the socket from which it was extracted because of geometrical interferences. There is a septum between the root recesses, and the recesses are not axially aligned. It is an object of this invention to provide an operative recess which can receive an implant suitable to replace much of the function of a multiply-rooted tooth.

There is another problem with osseointegrated implants which this invention intends to overcome. It is the possibility of bacterial entry into the recess which will lead to implant failure, and excessive height of the post, which enables the tongue and mastication to work at the implant and tends to loosen it. This invention attends to these problems.

Also, especially for single-crown implants, the abutments provide an important anti-rotation function.

BRIEF DESCRIPTION OF THE INVENTION

A support according to this invention comprises a post for supporting dental superstructures. Integral with the post, there is a set of legs. The legs are intended to fit into cavities formed in the bony structure so as to become osseointegrated with the bone, and are not intended to project above the bony structure. The legs are intended to fit in the bone, and may ultimately be osseointegrated and sometimes covered by bone. The leg or legs may extend laterally from the post so as to give support against tilting and working loose.

According to yet another preferred but optional feature of the invention, a plurality of posts are provided, joined by a longitudinal section to provide a support for more extensive dental superstructure.

The above and other features of this invention will be fully understood from the following detailed description and the accompanying drawings, in which:

DETAILED DESCRIPTION OF THE INVENTION

Figure 1:
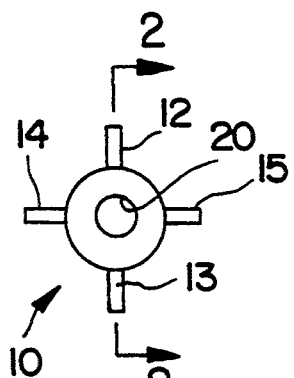
FIG. 1 is a top view of a single post implant according to the invention.

The utility of this invention is not limited to the lower jaw but instead is applicable to all jaw structures. Its intended purpose is to provide support for a crown or crowns, or for some other exposed dental superstructure such as a bridge denture. The supported structures are intended for chewing for aesthetic purposes.

Here it should be noted that the bony structure of the jaw consists of two kinds of bone. The outer layer of bone, the cortical bone, is very hard. Inside the cortical bone is a softer, somewhat pliable bone, the medullary bone. The medullary bone conducts fluids necessary for the function of the bone. It is quite vascular.

Suitable implant materials will osseointegrate with both types of bone. Experience has shown that it is advisable to provide for osseointegration with medullary bone as well as with cortical bone. However the thickness of the cortical bone varies widely from patient to patient, and the boundary between the two types of bone is often indistinct. Also, some patients have little or no medullary bone. This invention is useful in all circumstances.

The depth to which one may go into the bony structure in the lower jaw regardless of the type of bone in which the implant is to fit, is limited by the proximity of the mandibular nerve in the lower jaw. Accordingly in this invention advantage is taken of lateral support as the consequence of osseointegration with the bony structure. The situation is analogous for the upper jaw, for here the depth of acceptable penetration is seriously limited by the proximity of the maxillary sinus.

Further attention is called to some practical aspects of implantation. Tooth loss may be caused by invasion of the region between the tooth or implant and the bony structure. The tooth or implant and bony structure do not provide a seal against bacterial incursion. Instead this function is provided by gingival tissue—the gums. It is essential that this tissue cover the bone between the teeth, and that it closely embrace the tooth or implant structure where it projects above the bone. This embrace is where the protective seal is made.

In this invention, the only part of the implant which rises above the bony structure is a short post, located where a tooth may have formerly existed. Accordingly, existing tissue which had to be separated during the implantation procedure is simply returned to its place and sutured there, with a proper seal made around the post.

Further, another possible cause of implant failures has been the premature inclusion of a crown or a tall post as part of the implant when first implanted. In fact, some implants are provided as a single piece including the tooth crown or a tall post. Here the problem is that the tongue and mastication, which are very powerful, can work on the projecting part of the implant and by the resulting movement of the implant frustrate its osseointegration. In the practice of this invention, the post rises no higher above the gingiva than is necessary to form a complete seal with it.

Figure 2:
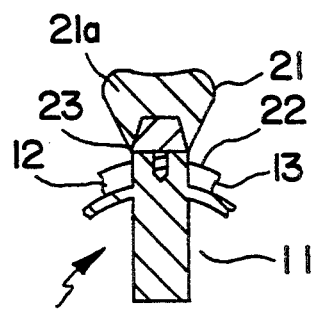
FIG. 2 is a cross-section taken at line 2—2 in FIG. 1.

FIGS. 1 and 2 shows an implant 10 suitable for replacement of a single tooth, although it will often be used as one part of a multiple part assembly to support a more elaborate superstructure. This implant includes an insert portion 11 which is intended to fit properly into an operative recess. Classically this recess can be the socket remaining after the extraction of a tooth. Portion 11 is not intended to duplicate the entire surface of an extracted tooth. The geometries of insertion of complex shapes of a tooth root make this too complicated. Besides, it is unnecessary. An implant can be retained by osseointegration with much less that total congruency of the entire tooth and socket. Instead, a lesser amount of contiguity is sufficient, and the recess may if desired be prepared by mechanical means, rather than by replacing an extracted tooth or part of a tooth.

Therefore insert portion 11 is shown as a cylinder although it could take any other desired shape. If only shallow penetration is possible, its length might be insufficient to provide sufficient retention by osseointegration. For this reason, legs 12, 13, and 14 are provided. It will be recognized that these legs can be formed in various shapes, and that four or fewer legs, perhaps only one or two, can be sufficient.

Generally, legs 12 and 13 are formed as a saddle to straddle the bony structure. If legs 14 and 15 are provided, they will usually be relatively flat and extend longitudinally along the jaw.

A threaded receptacle 20 is drilled and tapped into the post, later to receive a crown 21. A conical adapter 21a is threadedly attached to the post, and the crown can be cemented to it. This adapter facilitates the later attachment of the crown. The gingiva 22 is shown schematically in FIG. 2. The projecting portion 23 of the post rises just far enough above the bony structure to accommodate the gingiva and enable it to make a good seal with post.

The crown or other superstructures will not be attached until after the implant has been osseointegrated. The least possible length of projecting portion rises above the gingiva. Then the tongue cannot worry the implant until after the implant becomes stable, often after at least two to six months when the superstructure is attached. The adapter is attached after osseointegration is sufficiently advanced.

The implant of FIGS. 1 and 2 serves well for rather small systems. For more extensive, restorations, it may be better practice to combine more than one of these, and to connect them with runners which can themselves become osseointegrated. Such arrangements are shown in FIGS. 3–6.

Figure 3:
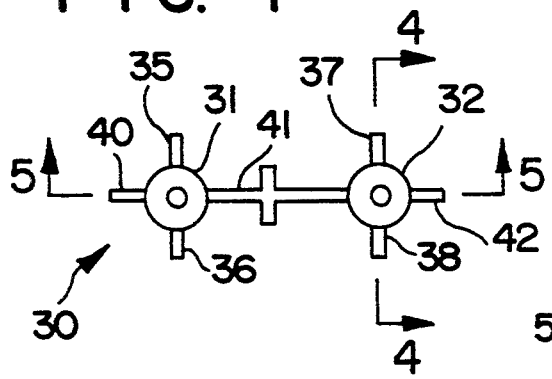
FIG. 3 is a top view of a multiple post implant according to this invention.

FIG. 3 shows an implant 30 which includes posts 31, 32 with the same properties as the post of FIG. 1. To illustrate the breadth of this invention, posts 31 and 32 are shown duplicating the shape of teeth extracted from a recess into which they are to be inserted. Often these shapes can be used, but not always.

Legs 35 and 36 are integral with post 31. Legs 37 and 38 are integral with post 32. These posts are saddle-like. Runners 40, 41 and 42 extend longitudinally relative to the posts. Runners 40 and 42 are similar to the other legs, but do not form a saddle. Runner 41 extends between the posts.

Figure 4:
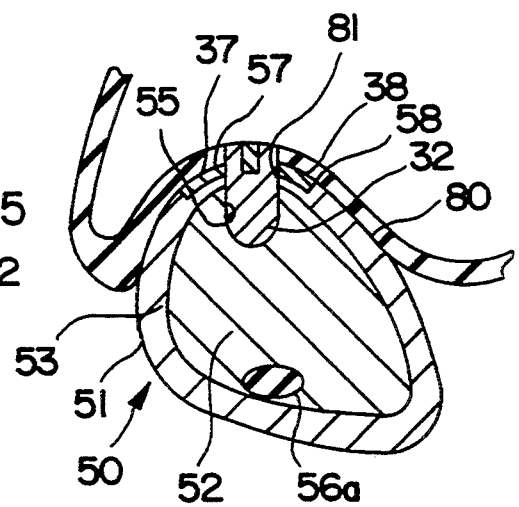
FIG. 4 is a cross-section taken at line 4—4 in FIG. 3, showing the implant of FIG. 1 implanted in a lower jaw.

As best shown in FIG. 4, the lower jaw 50 has bony structure with a cortical bone 51 and medullary bone 52. There is a theoretical interface 53 between them, which is sometimes not there, and is often indistinguishable.

Whatever the situation, post 32 has been fitted in recess 55. Observe its blunted end, to reduce the approach to the mandibular nerve 56a. The legs 37 and 38 fit in slots (recesses) 57, 58 in the bony structure. These slots are shown only in the cortical bone, but frequently they will extend into the medullary bone as will the legs.

Figure 5:
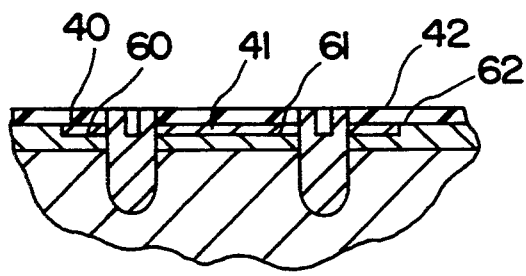
FIG. 5 is a cross-section taken at line 5—5 in FIG. 3.

FIG. 5 shows legs 40, 41 and 42 in respective slots (recesses) 60, 61, 62, again in cortical bone but optionally extending into medullary bone. Again in both situations the implant structure will fit in the major portion of the recess.

Figure 6:
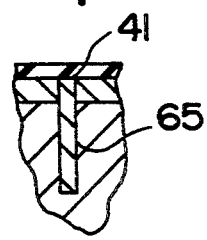
FIG. 6 shows a modified implant as in FIG. 3.

FIG. 6 shows a modification of FIG. 5 in which a blade-like extension 65 extends runner 41 farther into the bone additionally to stabilize the implant. In fact, it is shown extending into the medullary bone.

Figure 7:
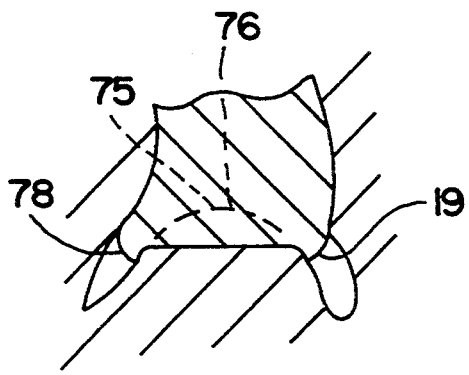
FIG. 7 is a schematic view of the socket from which a multiply rooted tooth has been extracted, showing a socket modification useful with this invention.

FIG. 7 illustrates the ,advantage of removing septum 75 from 24. The socket remaining after extraction of a tooth. The dashed line 76 shows material removed. Lines 78, 79 show advantageous removal of parts or all of the roots.

FIGS. 2 and 4 show an important feature of this invention. When implanted, no part of the implant projects above the surface 80 of the bony structure (FIG. 4) except the post, and this only through the gingiva, and only so far as required for the gingiva to make a seal 81 with the post. The tongue then cannot worry the implant, nor will mastication forces displace it. Except for this small projecting portion, this implant is fully received in the operative recesses (slots and sockets), and does not rise above the bony structure. Accordingly a relatively shallow post can effectively provide support for major superstructures.

Socket 50 is first prepared by the surgeon, and the pattern of the implant will be made from an impression of it. The slot is the complement of the illustrated implant. The lateral slots are cut primarily in the cortical bone. Depending on circumstances, these slots may or may not go into the medullary bone. One advantage of this invention is the support given to the lateral legs by the cortical bone.

However, some penetration into the medullary bone is usually considered to be useful. Because of the additional support, the posts can be made much shorter, and will not too closely approach the mandibular nerve, even when the bone has been considerably eroded.

When the center leg is used, the longitudinal leg can be made much wider so it can rest on a step in the longitudinal slot.

Whatever the construction, and whether the legs fit only in cortical bone of also in medullary bone, they will provide supplementary support to the implant that enables firm retention with minimal bony structure, and a close mandibular nerve.

In all situations the surfaces in the jaws will be prepared and an impression taken. The impression will be duplicated in a suitable material, or at least in a suitably-surfaced material to fit into the recesses, where they will be osseointegrated.

When the legs are provided, they act as anti-rotation means. Then forces which would tend to rotate the implant cannot do so. This feature can also be provided by shaping the cross-section of the implant non-circular. This feature is important for single crown installations.

It is also possible to form the legs and the remainder of the implant as separate parts and later join them such as by adhesives or screws.

Abutments to connect the implant to the prosthesis can be custom—made or commercially available abutments can be used. Accordingly, the total implant need not be made of one integral piece, but instead may be a joined assembly of pieces, as preferred.

In this invention, the recess into which the implant is to be fitted is frequently called a "defect". As such, a defect constitutes a discontinuity in the bony structure. As shown herein, the defect can be a socket from which a tooth has been extracted, or a surgically formed recess. In each case, further modifications will be formed to receive a lateral extension such as a leg, a runner, or some other extension from the insert portion. The lateral extensions fit neatly into the defect in substantial surface-to-surface contiguity to enable osseointegration to occur, because this is a custom implant formed as a casting derived from an impression of the defect. Neither the insert portion nor the lateral extensions rise above the surface of the bony structure. Only the post rises above the bony structure, and it does so only enough to enable gingival tissue to be sutured around it.

As a consequence, this invention significantly extends the utility of the earlier patented process and implant. It provides all of the advantages of osseointegration, while being useful in many situations where the use of the earlier process would not be indicated.

This invention is not to be limited by the embodiments shown in the drawings and described in the description, which are given by way of example and not of limitation, but only in accordance with the scope of the appended claims.

I claim:

1. A custom endosteal dental implant for implantation in a defect in bony structure of a human law, said bony structure being overlaid by gingival tissue, said gingival tissue having a dimension of thickness, said bony structure including cortical bone having an outer surface and underlying medullary bone, said defect extending through said surface and cortical bone and into said medullary bone, said defect having a boundary wall, and a lateral extension having a lateral extension wall extending away from said boundary wall, said lateral extension opening onto said surface so as to form a laterally-extending recess having a dimension of depth, said implant comprising a body having an outer implant surface, said outer implant surface comprising osseointegratable material, said implant including an insert portion so shaped as to fit snugly into a substantial proportion of said boundary wall in surface-to-surface contiguity therewith, and a lateral portion so shaped as to fit snugly in said laterally-extending recess in surface-to-surface contiguity with a substantial proportion of said lateral extension wall, all of said insert portion and of said lateral portion lying in said bone, beneath the said surface of said cortical bone, and a post portion having a dimension of height sufficient only in excess of the dimension of thickness of said gingival tissue sufficient to enable suturing of said gingival tissue around said post portion, the shape of said implant where it abuts bony structure having been derived from an impression of the defect.

2. A custom implant according to claim 1 in which said insert portion has an outer wall at least a portion of which is the geometrical complement of said substantial portion of said boundary wall of said defect.

3. A custom implant according to claim 2 in which said defect is at least a part of a socket which once held a tooth.

4. A custom implant according to claim 2 in which said laterally-extending recess extends transversely across the jaw.

5. A custom implant according to claim 4 in which said laterally-extending recess extends transversely across the jaw on both sides of said implant in a saddle-like manner.

6. A custom implant according to claim 2 in which said laterally-extending recess extends along the jaw.

7. A custom implant according to claim 1 in which said post is adapted to receive a next structure.

8. A custom endosteal dental implant for implantation in a defect in bony structure of a human jaw, said bony structure being overlaid by gingival tissue, said gingival tissue having a dimension of thickness, said bony structure including cortical bone having an outer surface and underlying medullary bone, said defect extending through said surface and cortical bone and into said medullary bone, said defect having a boundary wall, and a lateral extension having a lateral extension wall extending away from said boundary wall, said lateral extension opening onto said surface so as to form a laterally-extending recess having a dimension of depth, said implant comprising a body having an outer implant surface, said outer implant surface comprising osseointegratable material, said implant including at least two spaced apart insert portions each so shaped as to fit snugly into a substantial proportion of said boundary wall in surface-to-surface contiguity therewith, and a lateral portion integral with said insert portions joining them together so shaped as to fit snugly in said laterally-extending recess in surface-to-surface contiguity with a substantial proportion of said lateral extension wall, all of said insert portion and of said lateral portion lying in said bone, beneath the said surface of said cortical bone, and a post portion having a dimension of height sufficient only in excess of the dimension of thickness of said gingival tissue sufficient to enable suturing of said gingival tissue around said post portion, the shape of said implant where it abuts bony structure having been derived from an impression of the defect.

9. A custom implant according to claim 8 in which another lateral portion extends from each insert portion transversely across the jaw.

* * * * *